(12) United States Patent  
Suddaby (10) Patent No.: US 6,969,405 B2
(45) Date of Patent: Nov. 29, 2005

(54) INFLATABLE INTERVERTEBRAL DISC REPLACEMENT PROSTHESIS

(76) Inventor: Loubert Suddaby, 76 Tanglewood Dr., Orchard Park, NY (US) 14127

( * ) Notice: Subject to any disclaimer, the term of this patent is extended or adjusted under 35 U.S.C. 154(b) by 225 days.

(21) Appl. No.: 10/420,803

(22) Filed: Apr. 23, 2003

(65) Prior Publication Data

US 2004/0215342 A1 Oct. 28, 2004

(51) Int. Cl.$^7$ .............................................. A61F 2/44
(52) U.S. Cl. .................................................. 623/17.12
(58) Field of Search ........................ 623/17.11–17.16

(56) References Cited

U.S. PATENT DOCUMENTS

| | | | |
|---|---|---|---|
| 3,875,595 A | | 4/1975 | Froning |
| 4,772,287 A | * | 9/1988 | Ray et al. ................. 623/17.12 |
| 4,944,749 A | * | 7/1990 | Becker ........................... 623/8 |
| 5,047,055 A | * | 9/1991 | Bao et al. ................. 623/17.16 |
| 5,123,926 A | * | 6/1992 | Pisharodi ................. 623/17.13 |
| 5,514,180 A | * | 5/1996 | Heggeness et al. ....... 623/17.16 |
| 5,549,679 A | * | 8/1996 | Kuslich .................... 623/17.12 |
| 5,562,736 A | * | 10/1996 | Ray et al. ...................... 606/61 |
| 5,571,189 A | | 11/1996 | Kuslich |
| 5,674,295 A | | 10/1997 | Ray et al. |
| 6,019,792 A | * | 2/2000 | Cauthen ................... 623/17.14 |
| 6,022,376 A | * | 2/2000 | Assell et al. .............. 623/17.12 |
| 6,248,110 B1 | * | 6/2001 | Reiley et al. .................. 606/93 |
| 6,419,704 B1 | * | 7/2002 | Ferree ...................... 623/17.12 |

* cited by examiner

Primary Examiner—Eduardo C. Robert
Assistant Examiner—Annette Reimers
(74) Attorney, Agent, or Firm—Shoemaker and Mattare

(57) ABSTRACT

An intervertebral disc replacement prosthesis which can be implanted in a collapsed state, then expanded within the disc space such that minimally invasive surgical techniques may be employed for its insertion, and, by virtue of its expandable nature, ligaments can be restored to proper tension, facet joints can be unloaded posteriorly to inhibit degenerative changes, and functional mobility of the intervertebral segment can be restored.

3 Claims, 9 Drawing Sheets

Fig. 1a NEUTRAL POSITION

Fig. 1d NEUTRAL POSITION

Fig. 1b LATERAL BENDING

Fig. 1e FORWARD FLEXION

Fig. 1c LATERAL BENDING

Fig. 1f EXTENSION

Fig. 2a
NEUTRAL POSITION

NEUTRAL POSITION Fig. 2d

Fig. 2b
LATERAL BENDING

FORWARD FLEXION Fig. 2e

Fig. 2c
LATERAL BENDING

EXTENSION Fig. 2f

Fig. 3a NEUTRAL POSITION

NEUTRAL POSITION Fig. 3d

Fig. 3b LATERAL BENDING

FORWARD FLEXION Fig. 3e

Fig. 3c LATERAL BENDING

EXTENSION Fig. 3f

INFLATABLE INTERVERTEBRAL DISC REPLACEMENT PROSTHESIS

BACKGROUND OF THE INVENTION

This invention relates to orthopedic surgery, more particularly to a prosthetic intervertebral disc replacement system which can be implanted into a suitably prepared intervertebral disc space via minimally invasive surgical techniques to provide for and restore substantial functional normalcy.

The normal intervertebral disc is in essence a complex joint which allows for various articular motions between adjacent vertebral segments. These articular motions, in turn, account for the flexibility and functional mobility of the normal human spine. In the course of a day, the normal intervertebral disc encounters a variety of compressional, rotations and associated flexion or extension movements. In these day to day activities, movements in varying and repetitive combinations accumulate and contribute to the deterioration of natural discs that occurs over time. As with other joints in the human body that deteriorate over time, it would be desirable to have disc replacement prostheses which could be inserted in place of a failed or worn normal disc when it is determined the disc is irreparably damaged and that preservation of functional mobility is required. The time honored method of addressing debilitating symptoms and signs of a degenerative disc is to remove the disc and fuse the two adjacent vertebral bones together. Fusion eliminates motion at the abnormal segment, and while useful at improving debilitating symptoms, the consequence of eliminating natural motions at a single segment is that greater degrees of stress occur above or below that segment. This in turn accelerates degeneration of neighboring intervertebral discs, often necessitating additional fusion surgeries. It would be desirable, therefore, to preserve motion at every disc space and thus retain natural motion and eliminate the adjacent level degeneration that discectomy and fusion seems to produce. Toward this end, an intervertebral disc replacement prosthesis ought ideally to restore and preserve disc space height while permitting sufficient natural motion (flexion, extension, rotation and lateral bending) to prevent excessive stresses on spinal segments above and below the prosthesis.

Several intervertebral disc replacement prostheses are now in production, but none has the capacity to be implanted posteriorly through traditional exposures of the spine, or through smaller incisions, known collectively as minimally invasive surgical techniques.

SUMMARY OF THE INVENTION

An object of the invention is to provide for a complete and functional disc replacement that simultaneously restores sufficient disc space height and mobility to provide for functional normalcy, while allowing for a variety of surgical approaches and the use of minimally invasive surgical techniques.

To achieve this objective, the component parts of the replacement disc are bonded to the surface of sacks or chambers which are distensible or inflatable. In this manner, the replacement discs can be inserted through a small opening and then inflated within a disc space thereby assuming its final functional configuration. The sacks are nonporous and allow no escape of their contents. The sacks, or chambers, are initially inflated with a radio opaque liquid contrast material under fluoroscopic guidance to check for functional positioning and anatomic alignment, as well as functional integrity of the chambers themselves. Once ideal placement is confirmed, the radio opaque contrast material is removed and replaced with a hardenable material or resin which forms a solid construct once suitably mature. In this fashion, infinite anatomic variation of disc heights and configurations can be accommodated, and insertion of the replacement, disc can be facilitated through a small annulotomy favoring minimally invasive surgical techniques.

The preferred embodiment contains at least two inflatable chambers, although one, or any number of chambers might be conceived and created, depending on specific needs.

For example, in the two component version, one chamber sits atop the other with the disc space between the vertebral end plates. On the cranial or superior surface of the cranial chamber, teeth, digits, or corrugations are found which impress themselves into the end plate when the sack or chamber is inflated. A similar set of components is found on the caudal or inferior surface of the caudal or inferior chamber. These teeth or digits transgress the end plate surface and fixate the replacement disc in situ when the chambers are inflated. The juxtaposing surface between the cranial and caudal chambers contain mating surfaces that allow for functional motion between the cranial and caudal chambers when they are inflated to their final size. The mating surfaces are formed of male and female components that interdigitate, largely in a ball and socket fashion, but other similar functional relationships may be considered, provided that the adjacent surface interaction provides for the cardinal movements of a functioning intervertebral disc. These cardinal movements will allow for approximately 15 degrees of flexion, 5 degrees of extension, 5 degrees of lateral bending, 2 degrees of axial rotation and 1–5 mm of translation. When fully expanded, the fulcrum of movement on flexion and extension is located near the junction of the posterior one third and anterior two thirds of the vertebral body. The relationship between the components is such that it allows for varying degrees of rotation, flexion, extension and translational movements while simultaneously retarding the extremes of these motions to prevent disengagement of the cranial and caudal components at the extremes of functional movement. The mating surfaces are lined with polyethylene or similar materials suited for long term frictional wear. These linings may include plastics, ceramics, metals, carbon composites or combinations thereof.

The male and female component of the mating surface is bonded to the surface of its adjacent inflatable chamber such that proper union is assured when both chambers are inflated to their final proportions. Because the chambers are inflatable, they can be inserted into the disc in a collapsed state through a small opening and then inflated once they are appropriately positioned within the disc space.

As the chambers are inflated, teeth or digits on the superior or cranial and inferior or caudal surface of the chambers dig into the adjacent end plate and lock the prosthesis in position. The mating surface between the two inflated chambers in turn contains a ball and socket or male and female interacting component that permits functional movement between the cranial and caudal chambers when they are suitably inflated. By inflating them with a hardenable material, a solid, functional disc prosthesis can be formed with a final size that is much larger than its component parts. This allows not only for varying disc sizes and shapes, but also provides for use of the prosthesis in minimally invasive surgical techniques.

Suitable materials for the teeth or digits which bond to the end plate are any of a variety of metal or plastics or ceramics having sufficient strength to indent or puncture or bond with a vertebral end plate. Fabrics permitting tissue ingrowth might also be used.

Suitable materials for the walls of the inflatable chamber include Kevlar, polypropylene or any of a variety of plastics or fabrics having either elastic or non-elastic properties, but sufficiently pliable and having sufficient tensile strength to allow for deflated and inflated attitudes. The material should be sufficiently non-porous so as to prevent leakage of injected contents.

Suitable materials for the mating surfaces between the cranial and caudal chambers include any materials presently used in joint replacement having the capacity for long term frictional wear. These include various synthetics, such as polyethylene, plastics, ceramics and metal surfaces capable of long term cyclical frictional interactions.

Suitable materials to inflate the chamber to allow them to assume their final functional configuration include any hardenable material capable of maintaining function integrity under a variety of loads during various combinations of flexion, extension, rotation or translational movements. These materials include polymethyl methacrylate, polycarbonate, various polymerizing resins or indeed any material capable of being inject in a liquid or semisolid state and then capable of assuming a solid structural shape as determined by the recipient chamber into which it is injected.

In the simplest embodiment, a single chamber sitting between two metallic dishes conforming roughly to the shape of the vertebral end plates could be inflated to allow a friction fit of the metallic dishes to the end plates cranially and caudally. Once the injected material hardened within the chamber, functional mobility would be restored and retained.

In U.S. Pat. No. 3,875,595, Froning describes a bladder-like prosthesis which is inflated with liquid or plastic, but requires a valve as the material is non-hardenable and could potentially leak from the retaining bladder, causing the prosthesis to collapse.

Kuslich, in U.S. Pat. No. 5,571,189, describes an expandable porous fabric implant designed to stabilize a spinal segment. The fabric is porous and packed with biologic material which favors fusion of the interspace rather than functional mobility. It is packed with material which stabilizes a spinal segment by allowing ingrowth of bone and fibrous issues through pores on its surface.

In U.S. Pat. No. 5,674,295, Ray describes a pillow-shaped prosthetic spinal disc nucleus body made of a hydrogel core and a flexible constraining jacket which permits the hydrogel core to expand and contract. The constraining jacket is also porous, allowing entry and egress of fluids. the jacket is not filled with a hardenable material, since significant expansion and contraction is a pivotal feature to the biologic function of the prosthesis he describes.

These and other objects are attained by a inflatable intervertebral disc replacement prosthesis as described below.

BRIEF DESCRIPTION OF THE DRAWINGS

In the accompanying drawings.

DESCRIPTION OF THE PREFERRED EMBODIMENT

The drawings show several embodiments of the invention, having the characteristic feature that each prosthesis has at least one chamber which can be inflated to conform to various intervertebral spaces.

Preferably, each chamber is provided with studs, fingers, corrugations or other projecting structures designed to dig into the cranial and caudal surfaces of the vertebrae against which they bear, to keep the prosthesis in place. The chamber is at least partially made of a flexible material, not only so that it can expand, but also so that is can be collapsed to a small size, so that it can be inserted by minimally invasive techniques. The chamber wall may be a strong fabric material, for example Kevlar, or it may be made of a strong polymeric film such as polypropylene. In the case of Kevlar, which is not substantially stretchable, the chambers may advantageously be formed in a particular shape, which will be attained on inflation, corresponding to the particular space being filled.

Figure 2A:
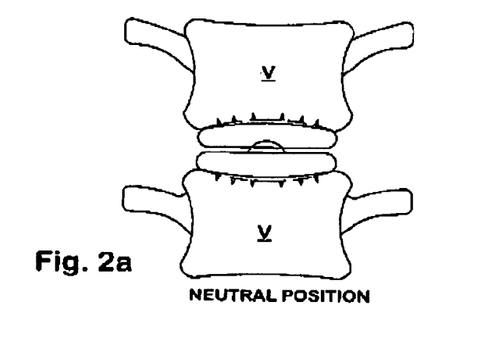
FIGS. 2a–2f are diagrammatic front and side views of a second embodiment of the invention.
Figure 2B:
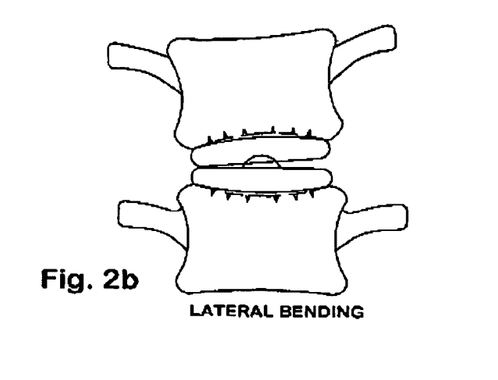
Figures 2C, 2F:
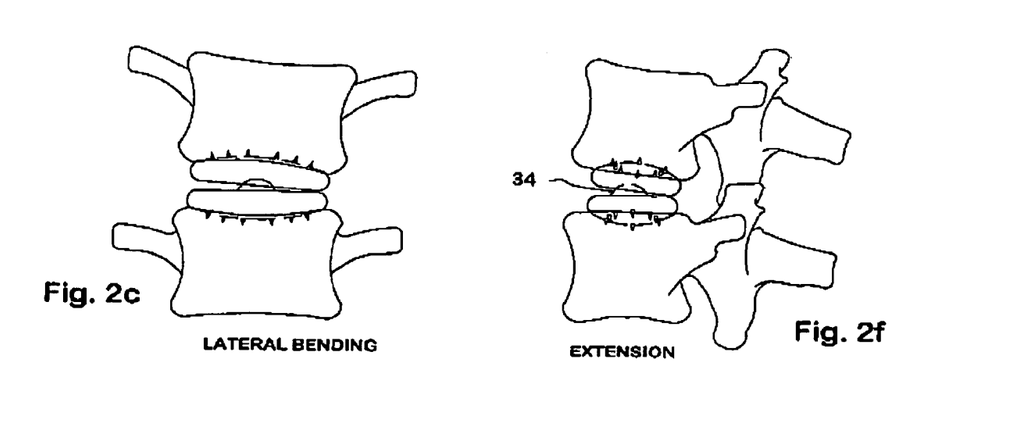
Figure 2D:
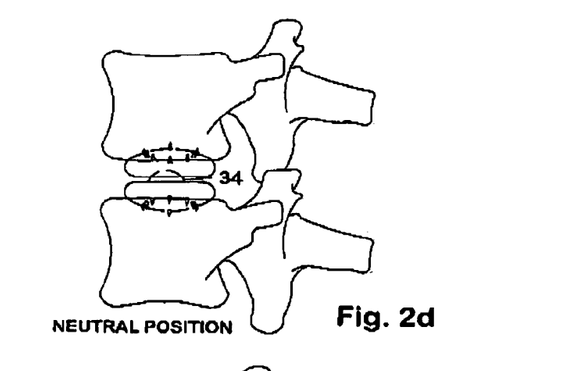
Figure 2E:
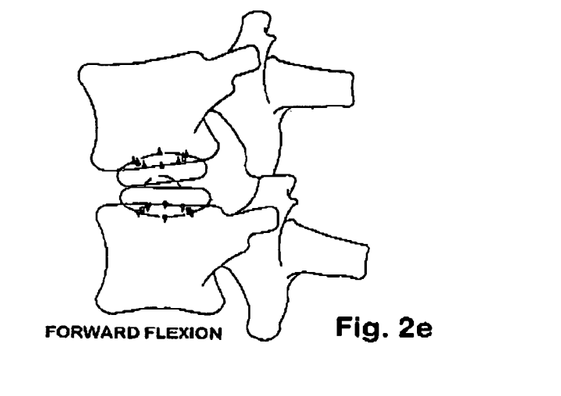
Figure 3A:
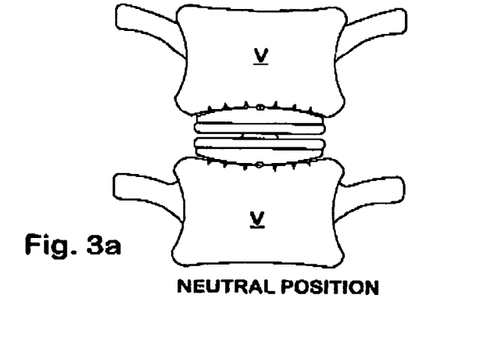
FIGS. 3a–3f are diagrammatic front and side views of a third embodiment of the invention.
Figure 3B:
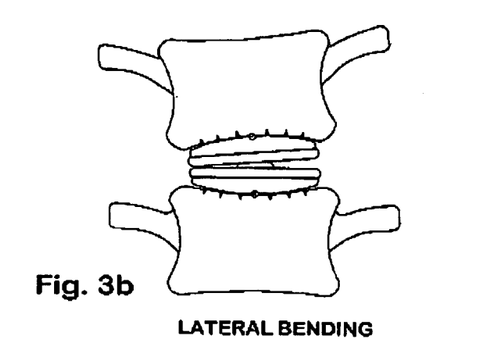
Figure 3C:
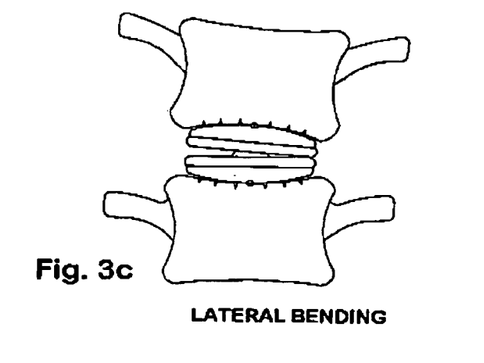
Figure 3D:
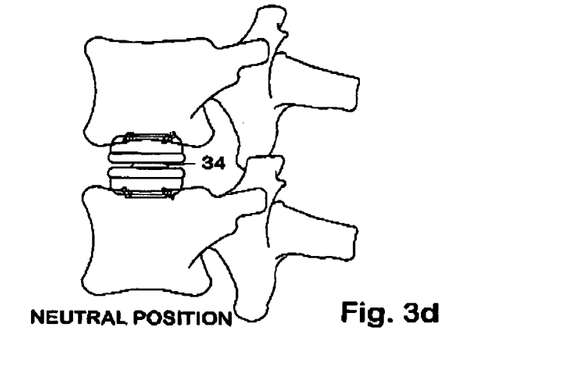
Figure 3E:
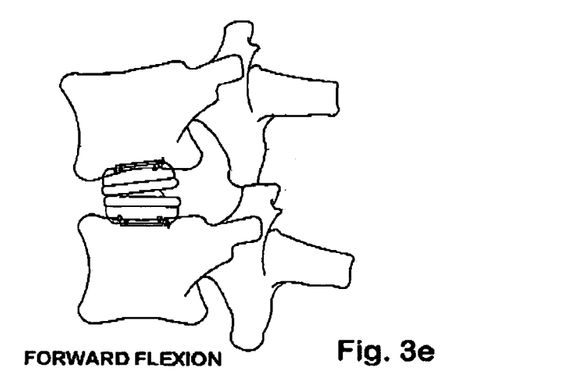
Figure 3F:
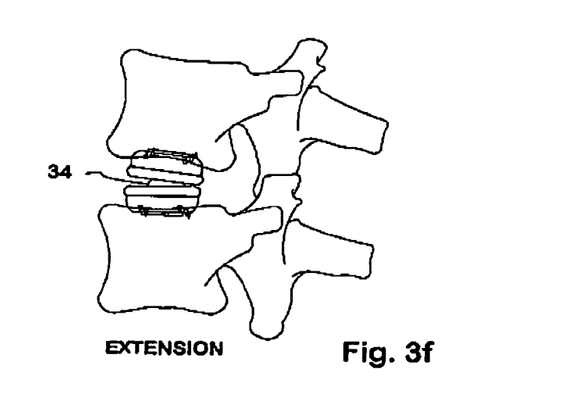
Figure 6A:
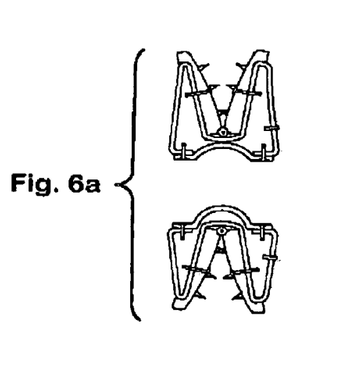
FIGS. 6a–6f are front and top view of a fourth embodiment of the invention.
Figure 6B:
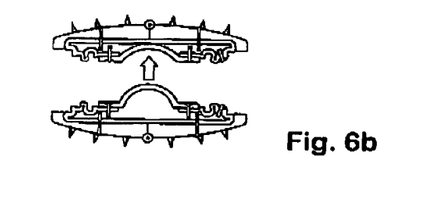
Figure 6C:
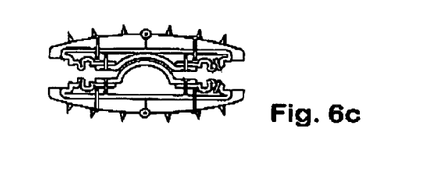
Figure 6D:
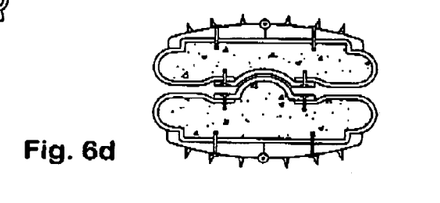
Figure 6E:
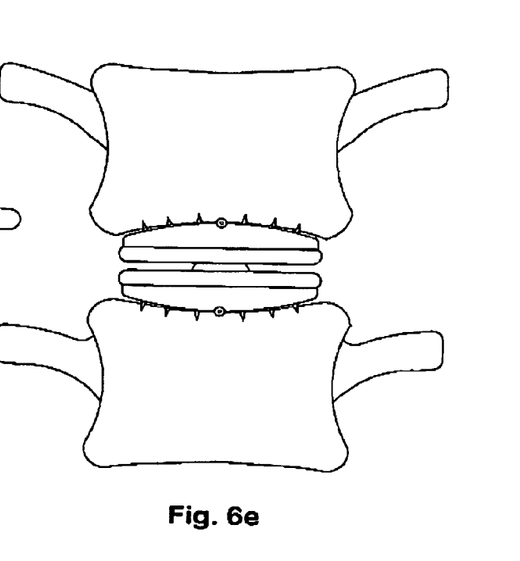
Figure 6F:
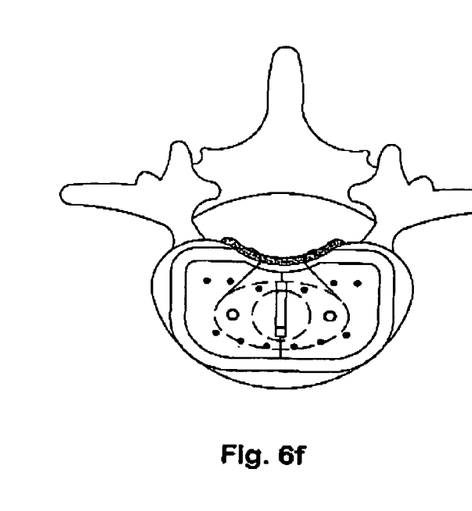
Figure 7A:
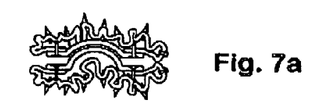
FIGS. 7a–7e are front and top views of the second embodiment of the invention.
Figure 7B:
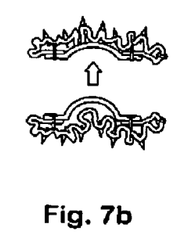
Figure 7C:
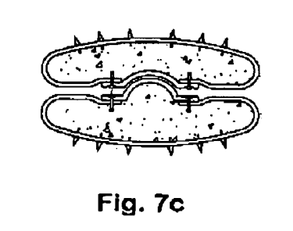
Figure 7D:
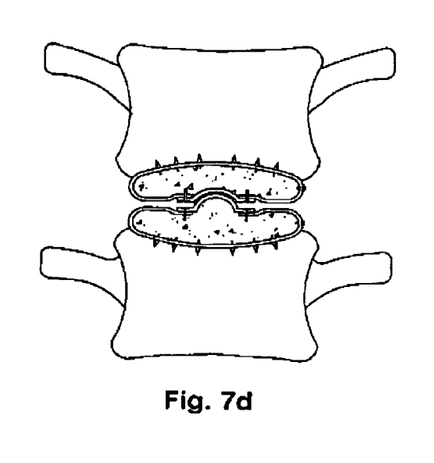
Figure 7E:
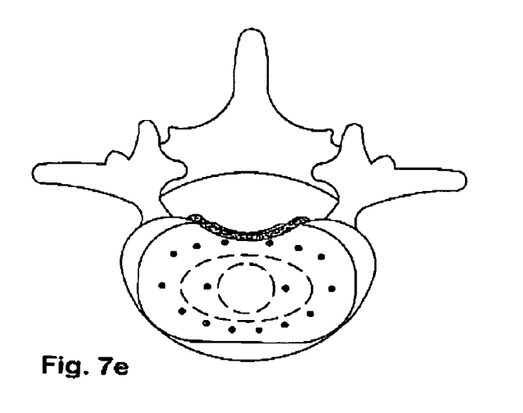
Figure 8A:
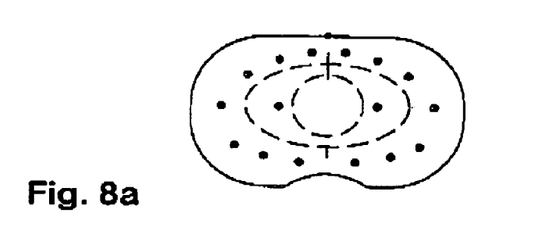
FIGS. 8a–8e are front, top and side views of a fifth embodiment of the invention.
Figure 8B:
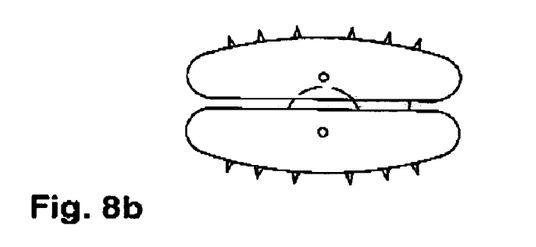
Figure 8C:
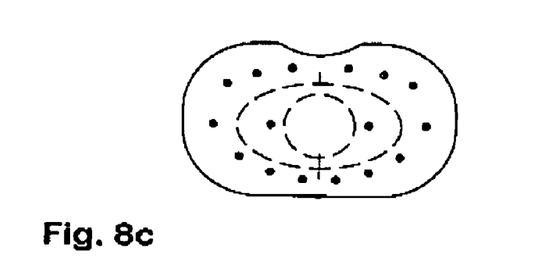
Figure 8D:
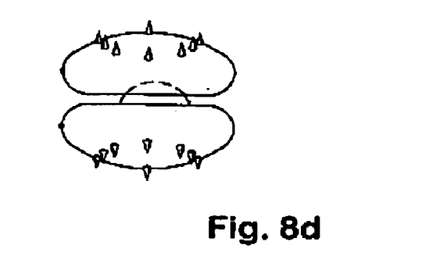
Figure 8E:
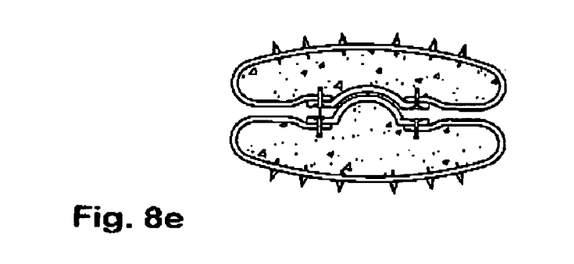
Figure 9A:
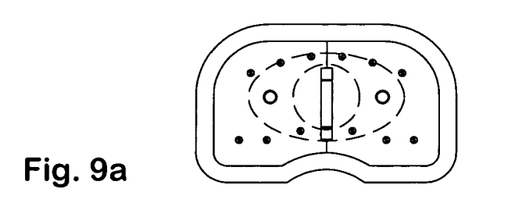
FIGS. 9a–9e are front, top and side views of a sixth embodiment of the invention.
Figure 9B:
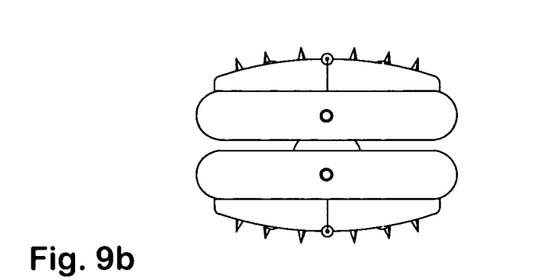
Figure 9C:
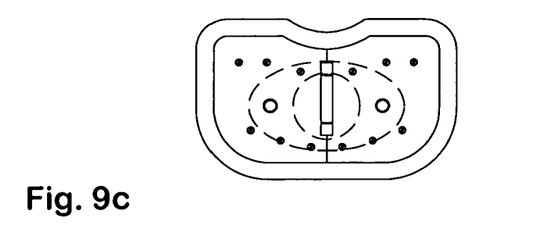
Figure 9D:
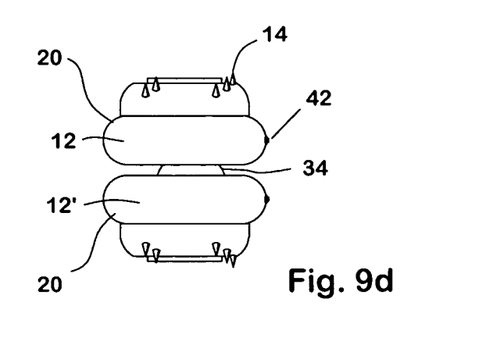
Figure 9E:
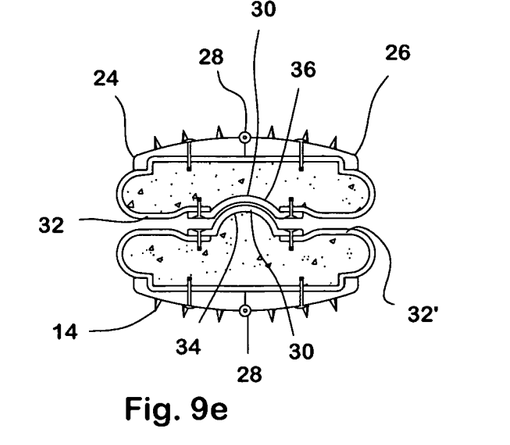

The chambers may have rigid end plates made, for example, of metal. FIGS. 2, 7 and 8 lack such end plates, and have the projecting structures formed integrally with the flexible wall material. In the other embodiments, the projecting structures are formed on the rigid end plates. Where the end plates are rigid, they may advantageously be formed in two or more parts, interconnected by hinges, so that they can be folded up to small size prior to insertion. Such constructions are suggested in FIGS. 3, 6 and 9.

Figures 1A, 1B:
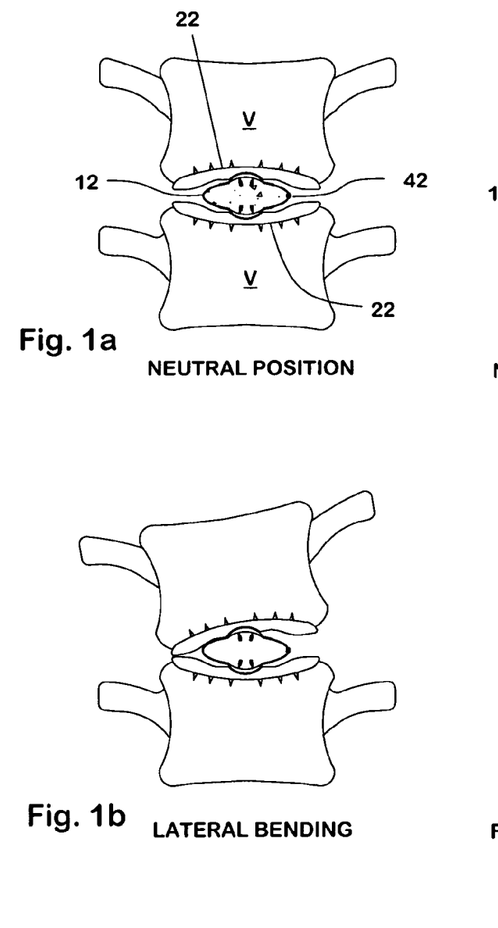
FIGS. 1a–1f are diagrammatic front and side views of an inflatable intervertebral disc replacement prosthesis embodying the invention.
Figure 1C:
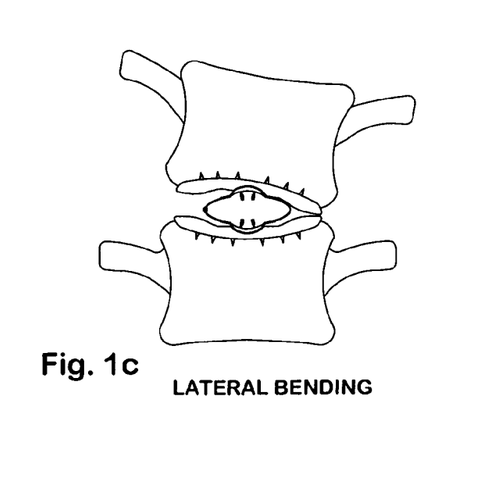
Figures 1D, 1E:
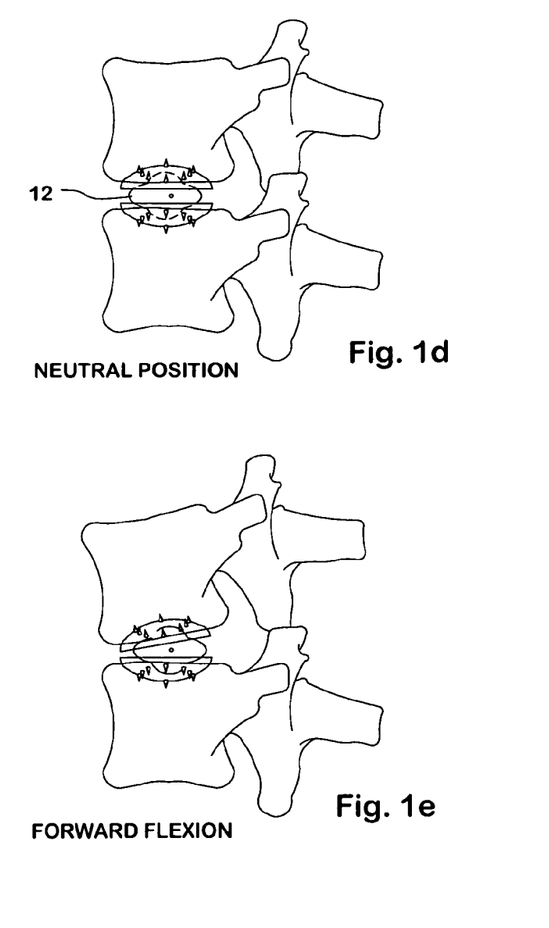
Figure 1F:
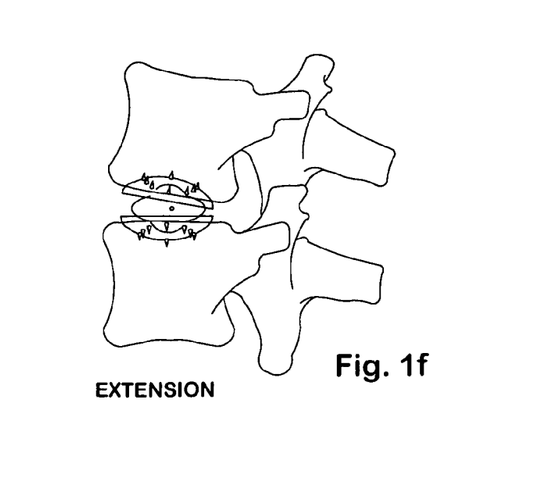
Figures 4A, 4B:
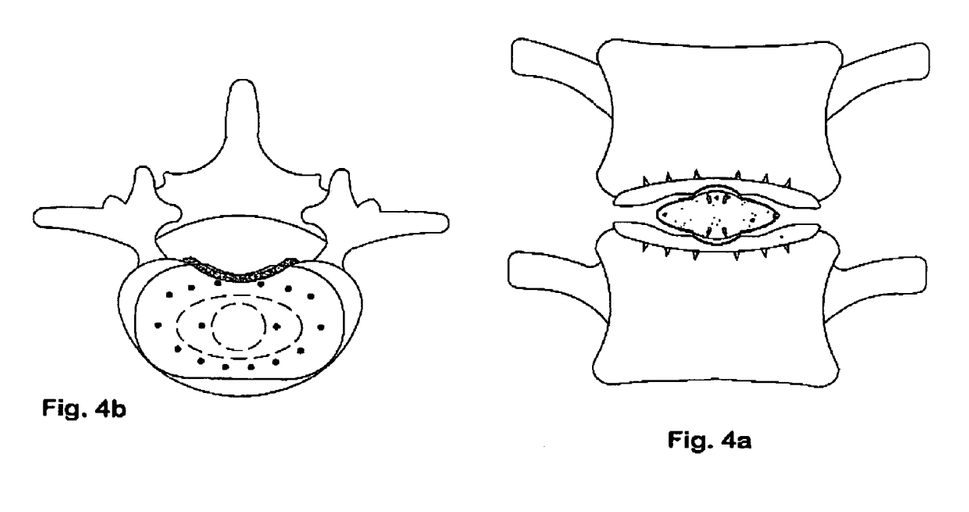
FIGS. 4a–4e are diagrammatic front and top views of the first embodiment.
Figure 4C:
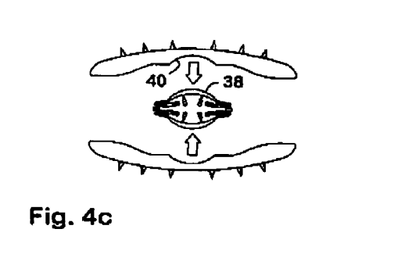
Figure 4D:
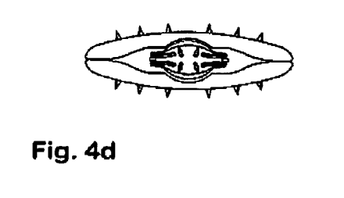
Figure 4E:
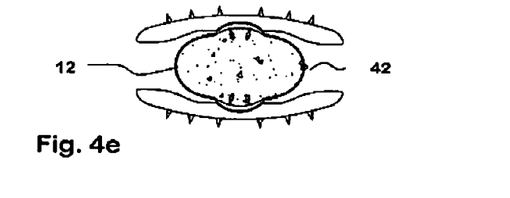
Figure 5A:
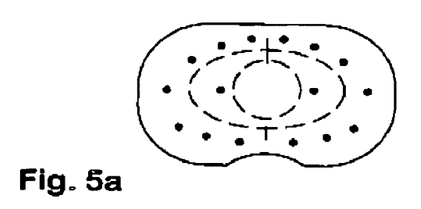
FIGS. 5a–5f are front, top and side views of the first embodiment.
Figure 5B:
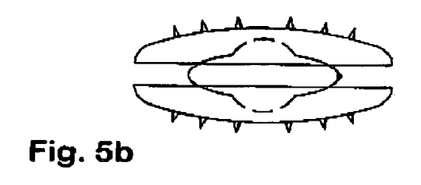
Figure 5C:
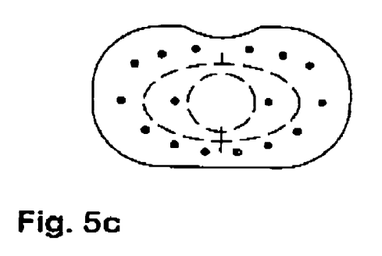
Figure 5D:
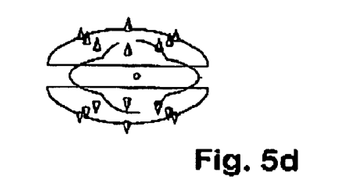
Figure 5E:
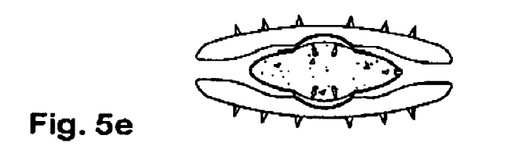
Figure 5F:
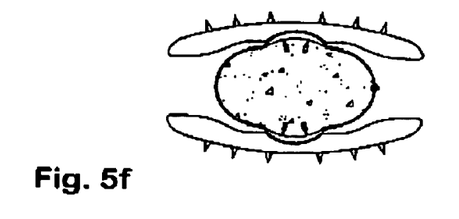

In the embodiments where two chambers are used (FIGS. 2, 3 and 6–9), the chambers may have an articulating joint between them, formed of cooperating rigid articular plates. The plates have complementary geometries, such as a ball and socket, to provide limited universal movement between the chambers. In the case of a single chamber (FIGS. 1, 4 and 5), there may be articular plates or portions designed to cooperate with correspondingly shaped recesses formed in the end plates.

In any case, the prosthesis is placed by first preparing the intervertebral space, then inserting the prosthesis in the space, and then inflating its chamber(s). The inflating fluid may be a liquid such as a gel or a hardenable material. Inflation is done to a degree determined by the surgeon to restore the space to its original height.

Since the invention is subject to modifications and variations, it is intended that the foregoing description and the accompanying drawings shall be interpreted as only illustrative of the invention defined by the following claims.

I claim:

1. An intervertebral disc replacement prosthesis comprising
 a pair of independently inflatable chambers, each adapted to engage a respective cranial or caudal surface of neighboring vertebrae,
 wherein said chambers have complementary structures which interengage to provide limited universal movement between said chambers, and
 said complementary structures are articular plates of a substantially rigid material, each of said plates being attached to a respective one of said chambers.

2. The prosthesis of claim 1, wherein one of said articular plates has a convex surface and the other of said articular plates has a corresponding concave surface.

3. The prosthesis of claim 2, wherein each of said convex and concave surfaces is substantially spherical.

* * * * *